United States Patent
Galloway et al.

(10) Patent No.: US 12,293,287 B2
(45) Date of Patent: May 6, 2025

(54) SYSTEMS AND METHODS OF IDENTITY ANALYSIS OF ELECTROCARDIOGRAMS

(71) Applicant: AliveCor, Inc.

(72) Inventors: Conner Daniel Galloway, Sunnyvale, CA (US); Alexander Vainius Valys, Sunnyvale, CA (US); David E. Albert, Oklahoma City, OK (US); Frank Losasso Petterson, Los Altos Hills, CA (US)

(73) Assignee: ALIVECOR, INC., Mountain View, CA (US)

( * ) Notice: Subject to any disclaimer, the term of this patent is extended or adjusted under 35 U.S.C. 154(b) by 328 days.

(21) Appl. No.: 18/085,427

(22) Filed: Dec. 20, 2022

(65) Prior Publication Data
US 2023/0131876 A1    Apr. 27, 2023

Related U.S. Application Data

(63) Continuation of application No. 15/914,337, filed on Mar. 7, 2018, now Pat. No. 11,562,222.
(Continued)

(51) Int. Cl.
*A61B 5/35* (2021.01)
*A61B 5/00* (2006.01)
(Continued)

(52) U.S. Cl.
CPC .............. *G06N 3/08* (2013.01); *A61B 5/341* (2021.01); *A61B 5/346* (2021.01); *A61B 5/35* (2021.01);
(Continued)

(58) Field of Classification Search
CPC ........... A61B 5/341; A61B 5/346; A61B 5/35; A61B 5/7221; G06N 3/04; G06N 3/08; G16H 40/63; G16H 50/20
See application file for complete search history.

(56) References Cited

U.S. PATENT DOCUMENTS

| | | | |
|---|---|---|---|
| 7,941,209 B2 * | 5/2011 | Hughes | A61B 5/7267 600/509 |
| 2014/0343957 A1 | 11/2014 | Dejori | |

FOREIGN PATENT DOCUMENTS

EP    1609412 A1    12/2005

OTHER PUBLICATIONS

International Search Report and Written Opinion received May 16, 2018 for International Application No. PCT/US2018/021309.

* cited by examiner

*Primary Examiner* — George Manuel
(74) *Attorney, Agent, or Firm* — WOMBLE BOND DICKINSON (US) LLP (57) ABSTRACT

A set of training electrocardiograms (ECGs) for each of a plurality of subjects is processed using a machine learning model to generate an output for each training ECG of each of the plurality of subjects. Training ECGs for each subject are labeled with an identity of the subject. A machine learning model is trained by comparing the output generated for each training ECG to a corresponding label of the training ECG to generate an identity model to identify ECGs of a first subject of the plurality of subjects. A first ECG is received from an ECG sensor and input to the identity model, which generates an output indicating whether the first ECG corresponds to the first subject. In response to the output indicating that the first ECG does not correspond to the first subject, a condition that the first subject has or may develop is determined based on the output.

20 Claims, 7 Drawing Sheets

Related U.S. Application Data (60) Provisional application No. 62/468,303, filed on Mar. 7, 2017.

(51) Int. Cl.
*A61B 5/341* (2021.01)
*A61B 5/346* (2021.01)
*G06N 3/04* (2023.01)
*G06N 3/08* (2023.01)
*G16H 40/63* (2018.01)
*G16H 50/20* (2018.01)

(52) U.S. Cl.
CPC ............ *A61B 5/7221* (2013.01); *G06N 3/04* (2013.01); *G16H 40/63* (2018.01); *G16H 50/20* (2018.01)

SYSTEMS AND METHODS OF IDENTITY ANALYSIS OF ELECTROCARDIOGRAMS

CROSS-REFERENCE TO RELATED APPLICATIONS

This application is a continuation of U.S. application Ser. No. 15/914,337 filed on Mar. 7, 2018 and entitled "SYSTEMS AND METHODS OF IDENTITY ANALYSIS OF ELECTROCARDIOGRAMS," which claims the benefit of U.S. Provisional Application No. 62/468,303 filed on Mar. 7, 2017, the entire contents of which are hereby incorporated by reference.

BACKGROUND

Electrocardiogram waveforms and some other biomedical recordings vary from one individual to another. Such variations of electrocardiograms can be caused by particular anatomical features of an individual's heart and body. Electrocardiograms of individuals may change over time even while still being considered medically normal.

DETAILED DESCRIPTION

Described herein are techniques for determining an identity of individuals based on monitoring of an electrocardiogram as well as using deviations in electrocardiograms of a particular individual to identify potential changes in a status or condition of that individual. Small changes in a subject's electrocardiogram recordings have been shown to vary due to a variety of factors, including day to day exercise, nutrition, and sleep. However, differentiation in a subject's electrocardiogram may also be indicative of changes in underlying physiology, which may be due to the development or worsening of medical conditions. For example and not by way of limitations, subclinical changes in an electrocardiogram, e.g. less or non-clinically perceptible changes in electrocardiogram morphology resulting in a clinical reading of a normal electrocardiogram a change in electrocardiogram morphology from one "normal" morphology to another "normal" morphology, may still indicate the development of an underlying condition. As electrocardiograms are typically recorded sporadically and analyzed visually by a healthcare provider, there is a significant risk that slight but potentially indicative changes in a subject's electrocardiogram recordings go unnoticed. For example, a change in a subject's electrocardiogram may be unnoticed due to human error, due to visually undetected changes in the electrocardiogram morphology, resulting in a clinical reading of a normal electrocardiogram.

Systems and methods as described herein may use a machine learning model to identify an individual based on an electrocardiogram. For example, an identity analysis system may receive an electrocardiogram from and electrocardiogram sensor, or other source, and analyze the electrocardiogram to determine whether it is associated with a subject. In some embodiments, the machine learning model may be trained using electrocardiogram training data that includes a subset of electrocardiograms that are associated with the subject and a subset of electrocardiograms that are not associated with the subject. The electrocardiograms may be labeled as belonging to the subject or belonging to another individual in a population. The machine learning model may then be trained to identify the individual based on received electrocardiograms. Training of a machine learning model is described further below. After the machine learning model is trained, a new electrocardiogram can be input into the machine learning model and the machine learning model can provide an output of whether the new electrocardiogram belongs to the subject. In some embodiments, the machine learning model may give a probability of the electrocardiogram belonging to the subject and can provide an indication that the electrocardiogram belongs to the subject if the probability is above a threshold value.

In some embodiments, the identity analysis system may use the probability to determine whether there is a potential change in a status or condition of an individual. For example, if a probability of an electrocardiogram matching a subject is below a threshold, the identity analysis system may provide an interface requesting confirmation that the electrocardiogram was in fact taken by the subject. In response to the machine learning model determining that the electrocardiogram is not that of the subject, an identity analysis system may take several different paths. For example, if the person is not the intended subject, then a notification or appropriate action (e.g., denying access) is made. Another example is that the subject has undergone potentially significant changes indicative of a health condition that may need attention. In such a case one or more of the subject, health professional, or family member is notified.

In some embodiments, a machine learning model comprises a neural network trained to analyze an electrocardiogram of a subject. In some embodiments of the neural network, the neural network structure is chosen by a designer and the behavior of the neural network is determined by the data used to train it. In some embodiments, for example, the neural network training data includes data associated with one or more conditions associated with certain subjects.

While training the machine learning model can be performed with a number of techniques, as further discussed below, generally the electrocardiogram data will be input with identity labels. For example, the subject's electrocardiograms may be labeled as such, and other electrocardiograms from other individuals may be labeled as not belonging to the subject. Depending on the type of machine learning model, the training electrocardiogram data may then be processed by a set of mathematical operations (e.g. addition, multiplication, convolution) involving weight matrices in a number of layers of the machine learning model. After processing, the machine learning model may then generate an output or prediction. The output or prediction is compared to the label (e.g., whether or not the electrocardiogram is from the subject) for the training data, the machine learning model may be updated, e.g., weight matrices may be updated using back propagation so that the final output of the model better approximates the correct label, or known data, during a next processing stage. The process is continued with additional training data or repeated with the same training data until the model converges.

In some embodiments, the electrocardiogram data associated with subjects in the training data may be read by an electrocardiogram sensor as a number of samples. These samples may be digitized for input to the machine learning model during both training and application. For example, the electrocardiogram may represent data read in over a period of time. In some embodiments, the electrocardiogram may operate at approximately 300 hertz, 60 hertz, 1000 hertz, or at another frequency of sampling to provide accurate data for the electrocardiogram. The electrocardiogram data may be read into the machine learning model in intervals of time. For example, the electrocardiogram data may be used as a 10 second input of data. In some embodiments, rather than a continuous string of data, an average heartbeat may be determined by detecting each heartbeat present in the electrocardiogram signal, aligning each heartbeat based on a common feature such as the R-wave, and averaging each beat to produce an average amplitude at different parts of the beat. This may reduce noise or signal artifact present in the electrocardiogram recording.

The process of training the machine learning model may be repeated for each electrocardiogram in the training data. For example, the training may be performed by inputting each electrocardiogram with a labeled identity classification into the machine learning model. The model may then be updated based on the difference between output prediction of the machine learning model and the correct output (the label), e.g., weight matrices are updated. The process may be repeated through all the electrocardiogram data multiple times until the outputs of the machine learning model are within a threshold of accuracy. For example, the threshold may be set as a certain percentage of identity labels of the electrocardiograms in the training data being predicted correctly. In some embodiments, the training data may include hundreds, thousands, tens of thousands, millions, or other quantities of electrocardiogram data. In some embodiments, the electrocardiogram data can include tens or hundreds of samples from a target subject and tens, hundreds, thousands, or more samples from other individuals.

While various machine learning models may be used, in some embodiments a convolutional neural net, a recurrent neural net, or a combination of a convolutional neural net and a recurrent neural net may be used. For example, a machine learning model may include 4 convolutional layers and 2 fully connected layers. In some embodiments, fewer or additional layers of different types may also be used. Furthermore, in some embodiments, drop out regularization, skip connections, max pooling, or other techniques may be used.

In an example, a neural net for determining potassium concentrations contains 11 convolutional layers and one final fully connected layer. The first convolutional layer operates on the electrocardiogram signal (one or more leads) and contains 64 filters, each with a width of 16. Subsequent layers contain 32 filters each with a width of 16. The stride of the filters for layers 1, 2, 4, 6, 8, and 10 is one, and the stride of the filters for odd layers from 3 to 11 is two. Dropout is implemented between all layers except the first two. Max pooling is implemented after layers 3, 5, 7, and 9. There are skip connections between layers 3 and 6, 5 and 8, 7 and 10, and 9 and the fully connected layer. Batch normalization is implemented between layers 3 and 4, 5 and 6, 7 and 8, 9 and 10, and 11 and the fully connected layer. The convolutional layers use the standard rectified linear unit non-linearity, and the final fully connected layer has no non-linearity. In some embodiments, other machine learning models can include fewer or additional layers, different dropout, max pooling, normalization, or other feature implementations, different numbers and sizes of filters, or changes to other parameters of the machine learning models.

An electrocardiogram may be described with a number of features. Some of the common features viewed during analysis of an electrocardiogram include a P wave, QRS waves commonly referred to as a QRS complex, and a T wave. Other features may also be viewed in different electrocardiograms of different individuals. Various medical conditions may have an effect on an individual's electrocardiogram. For example, certain conditions may change a slope, amplitude, duration, smoothness, or other characteristics of a feature of an electrocardiogram signal. Other biosignals may have specific features known to those skilled in the art.

These effects on the morphology of an electrocardiogram are sometimes subtle and not directly obvious to the human eye. In addition, changes to an electrocardiogram may not correspond to changes in an obvious component of the electrocardiogram waveform (e.g. QRS complex), but may instead correspond to one or more correlations between one or more small and/or apparently unrelated features of the electrocardiogram. In order to provide improved detection in changes of one or more conditions of a subject, changes in identity probabilities of the subject may be used to indicate such a morphology change.

After training, a subject's electrocardiogram data may be input into the machine learning model that determines whether the electrocardiogram matches the identity of the subject on which the machine learning model was trained. In some embodiments, the electrocardiogram may be applied as an input to the machine learning model in the same or similar manner as during training. For example, if ten second intervals of electrocardiogram data were used to train a machine learning system, the same type of electrocardiogram data may be input to the machine learning model to predict an identity probability of the subject. Similarly, if an average heartbeat was used over an interval for the training data, the same average heartbeat pre-processing may be applied to the data input into the trained machine learning model.

After the subject's electrocardiogram is input to the machine learning model, the machine learning model generates an output indicating whether it predicts that the electrocardiogram belongs to the subject. For example, the output may be an affirmative or negative that the electrocardiogram matches the subject or a probability that the electrocardiogram matches the subject. The identity analysis system may use that output for a number of purposes. For example, the identity analysis system may use it as at least a portion of identity verification for security purposes. In some embodiments the identity analysis system may not store the electrocardiogram or related diagnostic information in a record of the subject unless there is additional secondary verification that the electrocardiogram does in fact belong to the subject. For example, if the output of the identity analysis system predicts that the analyzed electrocardiogram does not belong to an expected user, the identity analysis system may request verification that the electrocardiogram does in fact belong to the user. Such verification may be a prompt to the user or require a password or other verification. If the user indicates that the electrocardiogram belongs to a different subject, then the electrocardiogram may not be provided to medical records or other records associated with the expected user. If the user indicates that the electrocardiogram does belong to the expected user, then the electrocardiogram and related data may be stored in medical records associated with the subject. The identity analysis system may also generate an alert or perform other processing to determine a reason for the divergence of the electrocardiogram.

In some embodiments, the identity analysis system may also determine that if the machine learning model does not recognize that the electrocardiogram is from the subject then there has been a change in a condition, state, or status of the subject that may need further analysis by a healthcare professional. For example, if the subject develops an arrhythmia the machine learning model may not recognize new electrocardiograms from the subject as being from the subject. Accordingly, the machine learning model may generate an output that the identity of the new electrocardiogram does not match the identity of the subject. However, by alerting the subject, medical practitioners, or others to the identity mismatch, an identity analysis system can potentially catch a change in condition or status of the subject before a human would.

In some embodiments, the average identity probability over multiple sensed electrocardiograms is determined. For example, in a series of multiple electrocardiograms taken over several days, a single electrocardiogram that does not match the subject's identity network may not significantly affect the average identity probability and may be ignored, for example, because it may represent only a temporary or transient change due to random variation that causes the electrocardiogram to differ from the subject's training recordings. However, a sequence or grouping of electrocardiograms that all do not match the subject's identity network may significantly reduce the average identity probability, and may indicate a significant and/or permanent change in the subject's electrocardiogram morphology.

In some embodiments, a machine learning model used by an identity analysis system may include an auto-encoder. An auto-encoder can include an encoder and decoder. The encoder may comprise multiple layers of a neural network that receives an electrocardiogram as an input. The encoder can then reduce the dimensionality of the electrocardiogram to a latent vector space. The decoder can then reproduce the electrocardiogram from the lower dimension vector space. In some embodiments, to train the auto-encoder, a training set of electrocardiograms is provided to the encoder. The encoder then generates a vector representation of the electrocardiogram that the decoder uses to reproduce the electrocardiogram as an output. The output of the decoder is then compared to the electrocardiogram that was input to the encoder. Based on the differences between the output electrocardiogram and the original electrocardiogram, the encoder and decoder may be updated. By repeating this process with each of the electrocardiograms in the training data a number of times, the auto-encoder may converge to a process wherein an electrocardiogram input to the auto-encoder can be reproduced (potentially with some loss) at the output of the decoder.

The identity analysis system can then use the latent space vector representation of an electrocardiogram input to the machine learning model to determine certain characteristics of the electrocardiogram. For example, for a target subject, a set of electrocardiograms may be provided to the machine learning model, the identity analysis system may then use the vector representation of the set of electrocardiograms to determine a location in the latent space that is associated with the subject. For example, different individuals may have their electrocardiograms cluster in different regions of the vector space. Accordingly, based on the set of electrocardiograms of the subject, a region of the vector space may be associated with the subject. Then, additional electrocardiograms received from the subject can be compared to that region to determine if there is a change in condition or status of the subject. For example, if the machine learning model generates a vector for a new electrocardiogram that is outside of the region expected for a subject, it may determine that the new electrocardiogram doesn't match the subject. The identity analysis system can then use that information in the same manner as discussed above with respect to a neural network determining whether an electrocardiogram matches a subject. While the regions are described above as associated with a region of the vector space generally, in some embodiments, the clusters may be in a subset of dimensions of the latent vector space. For example, if the latent space includes ten dimensions, the clustering of a subject in a subset of two or three dimensions of the ten dimensional space may be used by the identity analysis system to determine if the identity of a new electrocardiogram matches an identity of a subject.

In some embodiments, training of a machine learning model may be performed at a computer or server capable of large amounts of data processing. For example, a computing or server system may be used to train a machine learning model based on labeled electrocardiogram data. In some embodiments, after training, a machine learning model may be applied by a different computer system than used for training. For example, a computing system or server system may be used to train a machine learning model for an individual, however, after training, the machine learning model may be transferred to and used by an individual's personal computer, mobile device, smart phone, wearable computing device (e.g., smart watch or health band), or the like, where input data is supplied to the trained model via the personal computer, smart watch or wearable computing device. Of course, in some implementations, different servers, computer systems, personal computers, mobile devices, or the like may be used to perform any tasks as described herein, e.g., a distributed network.

Figure 1:
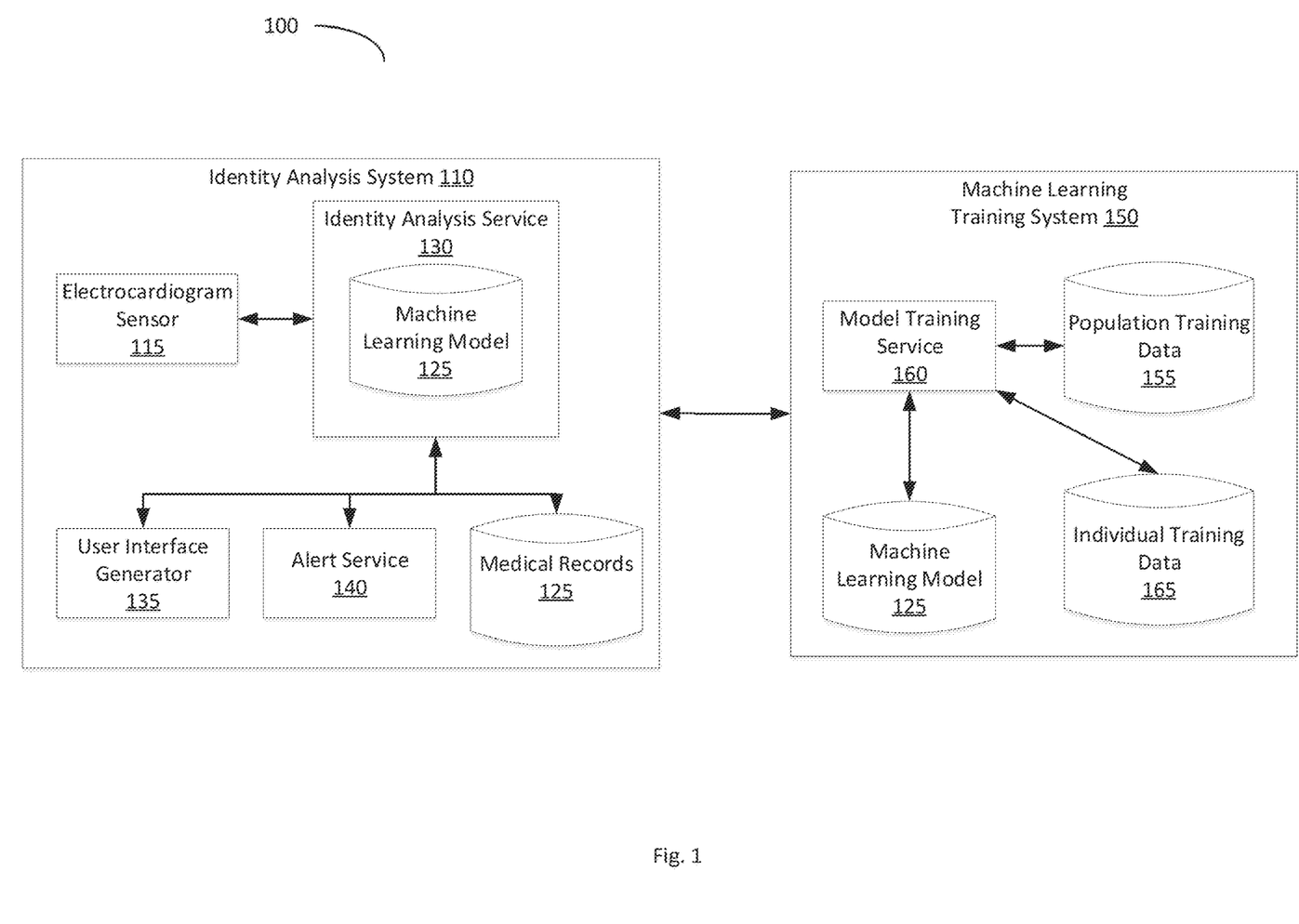
FIG. 1 illustrates an example system to provide identity analysis as discussed herein, according to aspects of the disclosure.

FIG. 1 illustrates an example system 100 that supports the analysis of electrocardiograms or other biosignals as described herein. The system 100 can include a machine learning training system 150 and an identity analysis system 110. The machine learning training system 150 can include a model training service 160 to train a machine learning model 125 using population training data 155 and individual training data 165. The identity analysis system 110 can include an identity analysis service 130 that provides data from an electrocardiogram sensor 115 as an input to the machine learning model 125. Based on the output of the machine learning model 125, the identity analysis system 110 can update medical records 125, provide alerts through alert service 140, or provide an interface through user interface generator 135. Although shown as separate components, in some embodiments, the identity analysis system 100 and the machine learning training system 150 may be part of the same computer system. In some embodiments, the identity analysis system 110 and the machine learning training system 150 may be remote components connected over a network. For example, the identity analysis system 110 may be located on a personal device such as a mobile device, personal computer, smart watch or wearable fitness band (collectively "wearable computing device"), or the like. The machine learning training system may be located on the same device as the identity analysis system 110 or on a remote device such as a central server.

In some embodiments, there may be fewer or additional components than shown in FIG. 1. For example, in some embodiments there may be additional identity analysis systems 110. Accordingly, additional identity analysis systems 110 may have different machine learning models 125 that provide identity predictions and analysis for a number of different subjects. For example, individual machine learning models 125 may be provided to a number of identity analysis systems at different computing devices to provide individual analysis for different subjects. Furthermore, while an electrocardiogram sensor 115 is shown as part of identity analysis system 100, in some embodiments, there may be different electrocardiogram sensors (not shown) that are used in different parts of training and application stages of a machine learning model 125.

The machine learning training system 150 may include model training service 160 population training data 155, individual training data 165, and machine learning model 125. The population training data 155 includes electrocardiograms taken from a number of subjects in a population. The electrocardiograms may include a segment of an electrocardiogram for each subject, e.g., a representation of 10 seconds, 30 seconds, 5 seconds, or another length of time of an electrocardiogram. Population training data 155 can be labeled as not belonging to a particular individual for which the machine learning model 125 is being trained.

The individual training data 165 includes electrocardiograms taken from a target subject for which the machine learning model 125 is being trained. The electrocardiograms may include a number of electrocardiograms from the subject, e.g., a representation of 10 seconds, 30 seconds, 5 seconds, or another length of time of an electrocardiogram. In some embodiments, the electrocardiograms in the individual training data 165 may be taken at intervals throughout a period of time to ensure that different conditions of the target subject are used for training the machine learning model 125. Individual training data 165 can be labeled as belonging to the target subject for which the machine learning model 125 is being trained.

The population training data 155, individual training data 165, and associated labels may be provided to a model training service 160 to train the machine learning model 125. In some embodiments, multiple electrocardiogram waveforms are averaged to form a single averaged waveform that serves as the input for the model training service 160. In some embodiments, the inputs may be an averaged waveform of heartbeats located within a set interval of electrocardiogram data. In some embodiments, the population training data 155 and individual training data 165 may be stored over a complete waveform interval. However, in some embodiments, additional pre-processing may be performed such as smoothing, noise reduction, or other processing. It should be understood, however, that any recording length as well as any other lead or combination of leads selected from leads I, II, III, aVR, aVL, aVF, V1, V2, V3, V4, V5, and V6 are suitable for use as inputs to model training service 160.

The machine learning model 125 may start as a generic machine learning model. For example, the machine learning model 125 may start with randomized values for a number of matrices within the model. The machine learning model 125 may be set with a number of convolutional layers, recurrent layers, or the like prior to training by the model training service 160. Non limiting examples of structural components of embodiments of the deep machine learning software described herein include: convolutional neural networks, recurrent neural networks, variational auto encoders, deep generative models, or Boltzmann machines.

In some embodiments, the machine learning model 125 may be a recurrent neural network. A recurrent neural network may receive sequential data as an input, such as consecutive electrocardiogram samples or beats, and then the recurrent neural network updates its internal state at every time step. In some embodiments the machine learning model may be a convolutional neural network. A convolutional neural network may include a number of convolutional layers that apply convolution operations using weight matrices and non-linearities to identify one or more features in the input data. The output of each convolutional layer may then be passed up to another layer to provide further analysis. In some embodiments, the machine learning model 125 may have a combination of recurrent and convolutional layers that identify and quantify different features in input data.

In some embodiments, the machine learning model 125 utilizes automatic statistical analysis of labeled data in order to determine which features to extract and/or analyze from a sensed biosignal (e.g. an electrocardiogram). The machine learning model 125 can to act as a function approximator, mapping a high dimensional input (raw electrocardiogram waveforms) into an identity probability. The machine learning model 125 determines which features to extract and/or analyze from an electrocardiogram based on the training that the deep machine learning software module receives.

In some embodiments, the machine learning model 125 can include an encoder component that encodes electrocardiograms into one or more values of latent space variables. The encoder can be trained using only the population training data 155 as described further below. A set of individual training data 165 can then be input into the encoder and the outputs can be mapped to a region of the latent space that identifies the target individual.

In some embodiments, electrocardiogram measurements described in latent space values can be used to both determine a subject's identity from a new electrocardiogram recording, and/or characterize the change in a subject's electrocardiogram when a new recording differs from the training recordings. For example, a variational autoencoder can be trained using training recordings from a subject, as well as other recordings taken from other subjects with known medical conditions, and the cluster of points in the latent space that correspond to recordings from that subject can be taken to be representative of that subject's identity. When a new recording from the subject is processed and found to be outside of the cluster of points that represent the training recordings, this may indicate a change in the subject's electrocardiogram morphology. The vector represented by the difference in the position of this new recording in the latent space, relative to the position of the training recordings, may be extrapolated to determine a medical condition that the user may have or develop.

The model training service 160 may train a model based on each of the labeled electrocardiograms in the population training data 155 and the individual training data 165. In some embodiments, the model training service 160 uses automatic statistical analysis of labeled data in order to determine which features to extract and/or analyze from a sensed biosignal (e.g. an electrocardiogram). The model training service 160 may determine which features to extract and/or analyze from an electrocardiogram based on labeled electrocardiogram training data 155 that it receives.

In some embodiments, the model training service 160 may be configured to receive a certain length of raw electrocardiogram data as an input. For example, an input to the model training service 160 may be 10 seconds or more of an electrocardiogram signal from lead I of an electrocardiogram sensor 115. In some embodiments the model training service 160 may use the untrained machine learning model 125 as a function approximator, mapping a high dimensional input (the raw electrocardiogram waveform) into a classification for the data (e.g. a probability that the electrocardiogram belongs to an individual). Based on differences between the classification generated as an output by the machine learning model 125, the model training service 160 may update the machine learning model 125 to better fit the labeled data.

The model training service 160 may provide each electrocardiogram in the population training data 155 and the individual training data 165 to the machine learning model 125 until the machine learning model 125 predicts the labels with sufficient accuracy. For example, the model training service 160 may determine that the machine learning model 125 has converged if it can correctly predict a threshold number of labels in the population training data 155 and the individual training data 165 correctly. In some embodiments, only some of the population training data 155 and the individual training data 165 may be provided to the model training service 160 to train the machine learning model 125 and the remaining the population training data 155 and the individual training data 165 may be reserved as a verification set. The model training service 160 may then verify the accuracy of the machine learning model 125 by testing the model on the verification set.

In embodiments using an auto-encoder, a model training service 160 can train a machine learning model 125 using only the population training data 155. The machine training service 160 can input electrocardiograms into the machine learning model and compare the output of the machine learning model to the input electrocardiogram. Neural network layers of the machine learning model 125 may then be updated based on the difference between the input electrocardiogram and the output of the machine learning model. After training, the auto-encoder can then generate a latent space representation of input electrocardiograms that is generated by the encoder portion of the machine learning model 125. The individual training data 165 can then be input to the machine learning model 125 and a region associated with the target subject in the latent space can be identified. For example, a number of vectors in the latent space can be generated for different electrocardiograms of the subject. New electrocardiograms can then be compared to a region in the latent space associated with the output vectors generated by the machine learning model 125 in response to the individual training data 125. The proximity of the electrocardiograms to the identified regions can indicate a probability that an electrocardiogram is associated with the target individual.

After a machine learning model 125 has been generated and verified, it can be provided to the identity analysis system 110. For example, as the machine learning model 125 is trained on the population training data 155 and the individual training data 165, it can be used on electrocardiograms not stored in the population training data 155 and the individual training data 165, which are input into machine learning model 125 to predict a subject's identity. In some embodiments, the electrocardiograms input into machine learning model 125 may be used by machine learning training system 150 to retrain a machine learning model 125 to improve the model. As a new machine learning model 125 is generated, it may be pushed as an update to identity analysis system 110.

The identity analysis system 110 in FIG. 1 may include an identity analysis service 130 to input data from an electrocardiogram sensor 115 machine learning model 125. In some embodiments, the electrocardiogram sensor 115 may be separate from the identity analysis system 110 and may provide an electrocardiogram segment remotely to the identity analysis system 110. The machine learning model 125 may be the same as was trained by machine learning system 150. In some embodiments, the machine learning model 125, the identity analysis service 130, or other components of the identity analysis system 110 may be on a separate computing system than the identity analysis system 110. For example, the machine learning training system 150 may have one or more components of the identity analysis system 110.

The identity analysis system 130 may apply the machine learning model 125 by inputting a segment from electrocardiogram sensor 115 to the machine learning model 125. As discussed herein, the electrocardiogram data may be pre-processed into set interval segments, average heartbeats, smoothed, noise reduced, or otherwise provided in a set manner to the machine learning model 125. The identity analysis service 130 may then input a segment of electrocardiogram data to the machine learning model 125 to generate an output of an identity probability. The electrocardiogram data input to the machine learning model 125 may be provided in the same manner as the population training data 155 or individual training data 165 used to train the model. For example, if the population training data 155 was provided as ten second segments, the identity analysis service 130 provides a ten second segment of electrocardiogram to the machine learning model 125.

Based on the output of the machine learning model 125, identity analysis service 130 can initiate one or more operations. For example, if the machine learning model 125 outputs a probability over a threshold that the identity matches a target subject, identity analysis service 130 can store the electrocardiogram and any related analysis in medical records 125 associated with the target subject. If the identity analysis service 130 determines that the machine learning model 125 output is below a threshold identity probability, it can display or provide one or more user interfaces through a user interface generator 135 or alerts through alert service 140. For example, the user interface generator 135 can provide an interface confirming the identity of the subject, providing an indication of a possible change or condition, or otherwise indicating to the user of the electrocardiogram sensor 115 that there may be an emerging change in the user's electrocardiogram. The alert service 140 can generate an alert to a medical practitioner, family member, or other individual indicating that there may be a change in the status of the user based on the lack of matched identity. For example, a record of the electrocardiogram can be sent to a medical practitioner or to other machine learning models to determine one or more conditions associated with any change in the electrocardiogram compared to other records of the subject.

Figure 2:
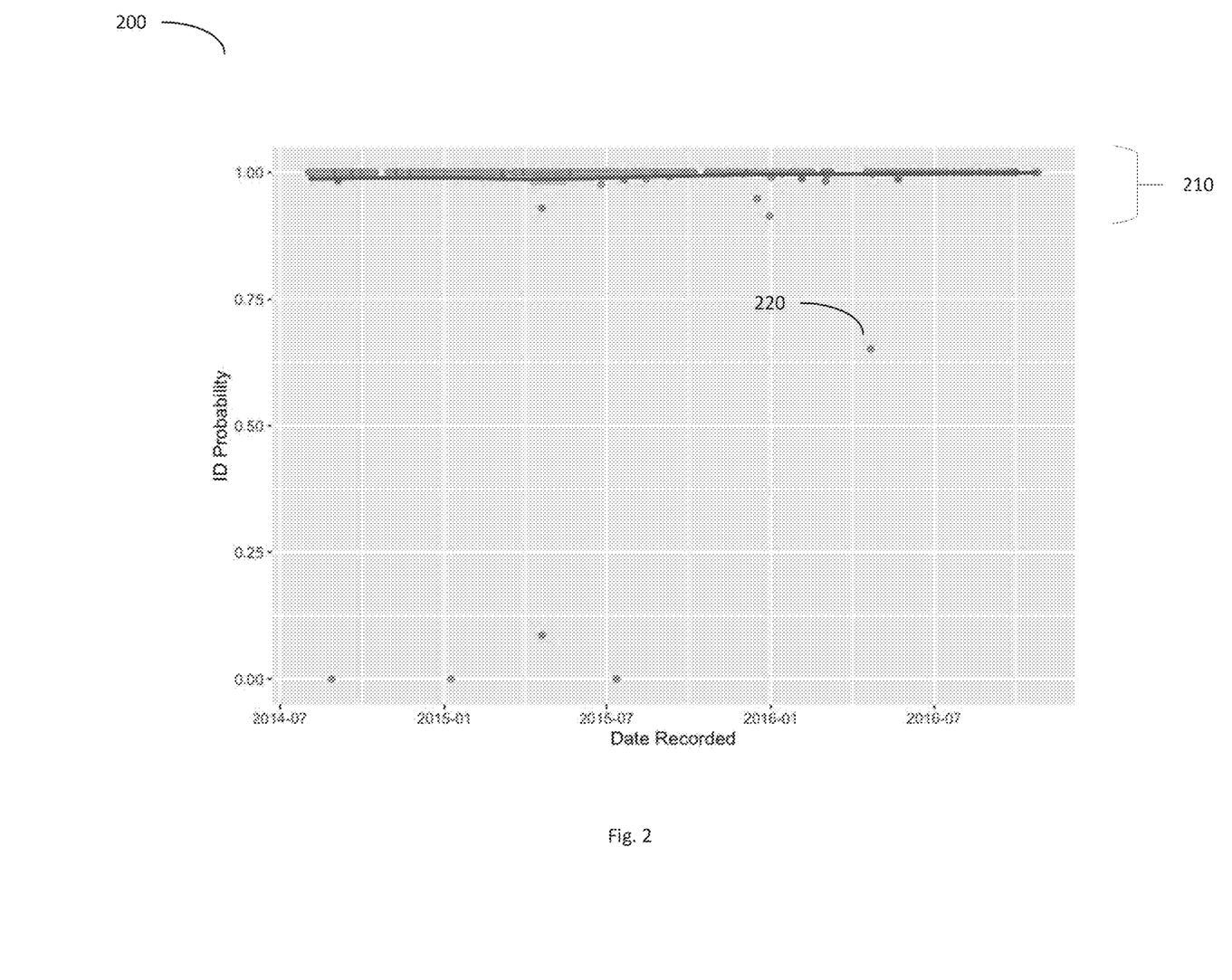
FIG. 2 illustrates a chart illustrating example outputs of an identity analysis system, according to aspects of the disclosure.

FIG. 2 shows an exemplary chart 200 of outputs of a machine learning module that has been trained on electrocardiogram recordings for a subject. The exemplary outputs shown in chart 200 results output from a machine learning model in response to electrocardiogram input for the subject over a period of time. Each point shown in chart 200 represents the identity probability (on the vertical axis) for an individual recording taken on a specific point in time (on the horizontal axis). In some embodiments, the machine learning outputs in chart 200 may be generated by an identity analysis service 130 as described with reference to FIG. 1. As shown in FIG. 2, the majority of the outputs are within a confidence range 210 near the top of the identity probability range. There are also some outputs that show a lower identity probability. For example, output 220 has a lower identity probability than confidence range 210. In some embodiments, an identity analysis system may confirm the identity of the user, issue an alert, or provide other feedback in response to the lower probability. In some embodiments, an identity analysis system may not provide feedback until there are additional lower probability outputs. The sporadic lower identity probabilities in FIG. 2 may have been caused by short temporal abnormalities of the subject such as recent exercise, sleep, sickness, nutrition, or other factors.

Figure 3:
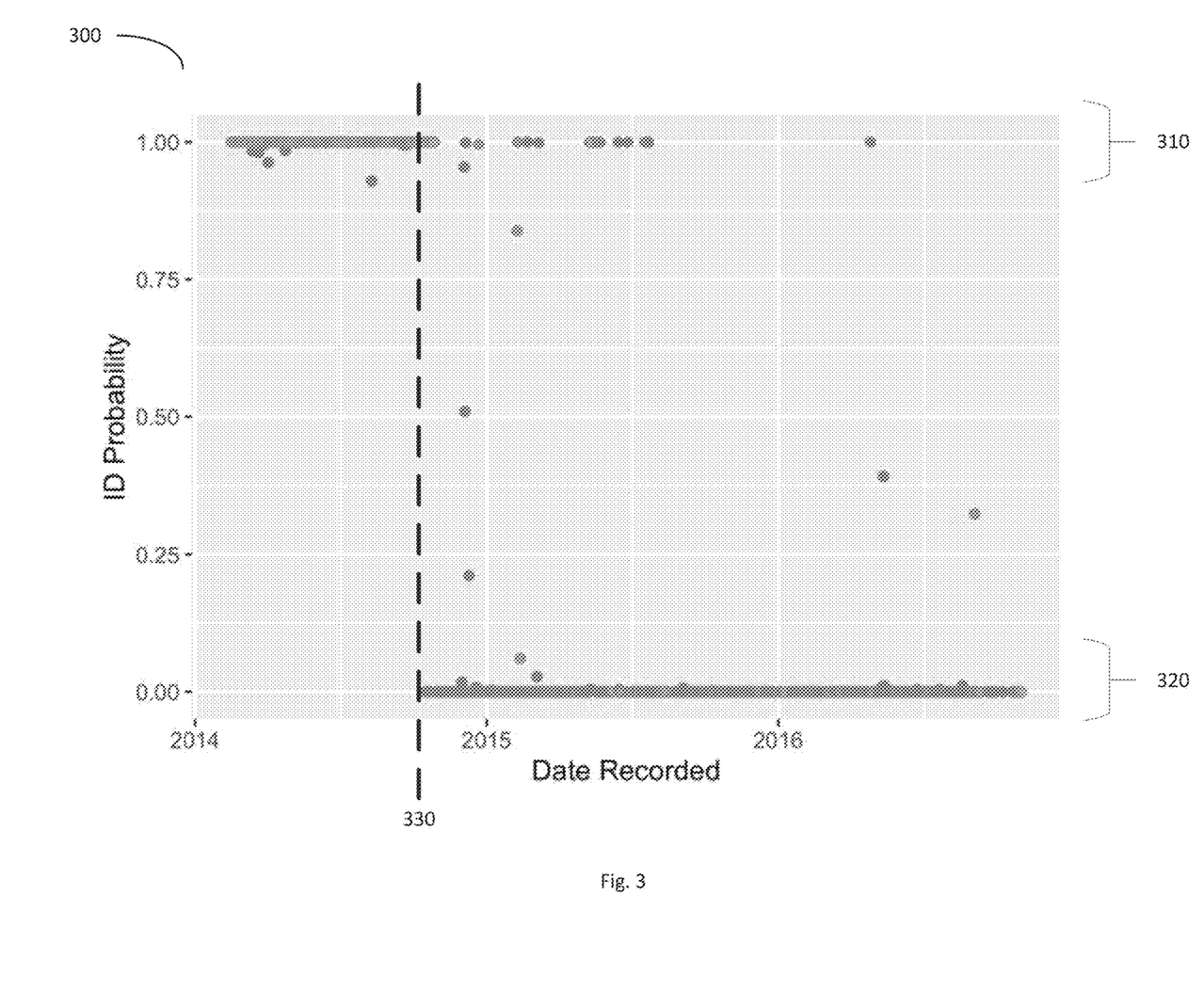
FIG. 3 illustrates a chart illustrating example outputs of an identity analysis system, according to aspects of the disclosure.

FIG. 3 shows another exemplary chart 300 of outputs of a machine learning module that has been trained on electrocardiogram recordings for a subject. The exemplary outputs shown in chart 300 are from a machine learning model in response to electrocardiogram input for the subject over a period of time. Each point shown in chart 300 represents the identity probability (on the vertical axis) for an individual recording taken on a specific point in time (on the horizontal axis). In some embodiments, the machine learning outputs in chart 300 may be generated by an identity analysis service 130 as described with reference to FIG. 1. As shown in FIG. 3, the majority of the outputs at the beginning of the shown time window are within a confidence range 310 near the top of the identity probability range. However, after a certain point in time 330, the majority of the outputs are near a low identity probability. This may indicate a change in condition or status of the subject after the time represented by point 330. The biosignal recordings with an identity probability of 0% or essentially 0% are determined by the machine learning module to be outside the normal variation in electrocardiograms within the training set for the subject. For example, the subject may have developed a permanent change in their electrocardiogram relative to the morphology represented by training set. Or, for example, the subject may share the system described herein with a spouse or other family member, and the sensed biosignal of the spouse or family member is determined to have a 0% or essentially 0% identity probability.

Figure 4A:
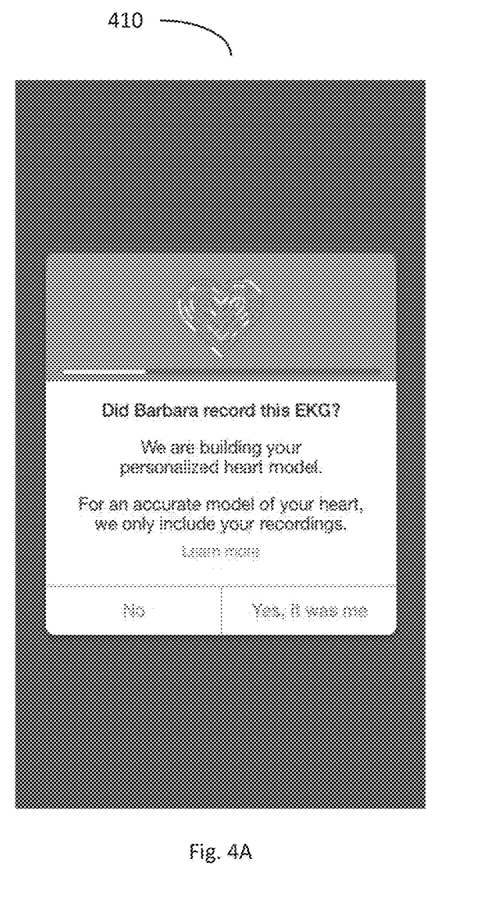
FIG. 4A illustrates an example user interface as generated by an identity analysis system as discussed herein, according to aspects of the disclosure.
Figure 4B:
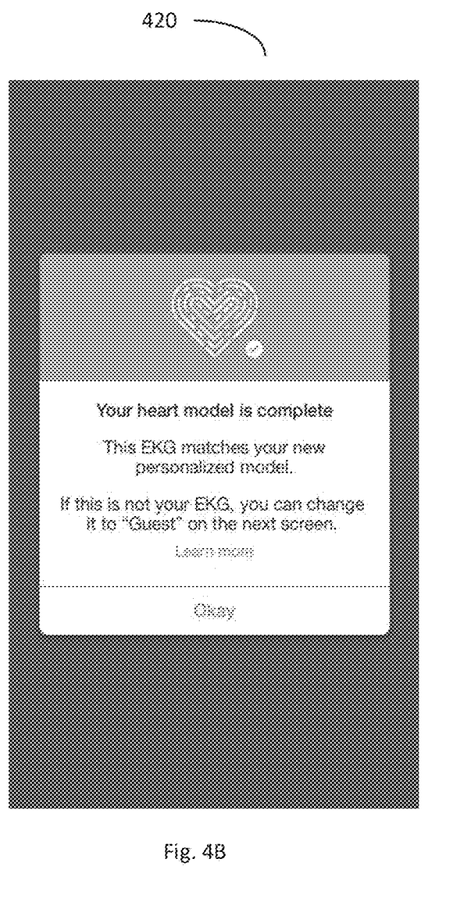
FIG. 4B illustrates an example user interface as generated by an identity analysis system as discussed herein, according to aspects of the disclosure.
Figure 4C:
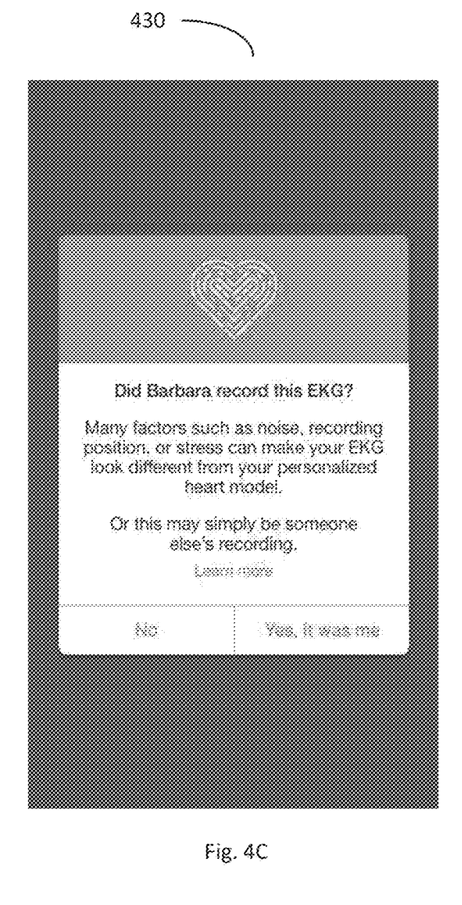
FIG. 4C illustrates an example user interface as generated by an identity analysis system as discussed herein, according to aspects of the disclosure.

FIGS. 4A-4C depict example user interfaces 410, 420, and 430 showing aspects of an identity analysis system as described herein. For example, in some embodiments the user interfaces 410, 420, and 430 may be generated by user interface generator 135 as described in FIG. 1. The user interface 300, or variants thereof, may be displayed on a mobile device, a personal computer, a web browser, a smart watch, or other computing devices.

In FIG. 4A, the user interface 410 prompts a user to determine if an electrocardiogram was taken by the user. The user interface 410 may be used to ensure individual training data for training a machine learning model uses accurate labels. For example, if the user indicates that they are the subject, then the electrocardiogram may be stored in a set of electrocardiograms to be used for training the machine learning model and may be labeled as belonging to the target subject. If the user indicates they are not the target subject, the electrocardiogram can be labeled as not from the target subject and used as another training set, or the electrocardiogram may be discarded.

In FIG. 4B, a user interface 420 indicates that an identity model is complete for an individual. For example, model training service may determine that a threshold number of electrocardiograms of a subject have been collected to train the machine learning model. In some embodiments, the threshold of electrocardiograms may be a set number, a set number over a span of a number of days, a set number taken in different circumstances or times of days, or another threshold set of electrocardiograms. After the identity model is complete, the user can then use the identity model for security, identification, determination of changes status or conditions, or other applications as described herein.

In FIG. 4C, a user interface 430 prompts a user in response to the identity probability generated by a machine learning model being below a threshold level. For example, as shown in user interface 430, the user is prompted to confirm their identity. In response a user can confirm their identity or indicate that it is somebody else. If the user confirms their identity, the identity analysis system may determine if a number of incorrect identities have occurred in a set amount of time and alert the user with additional information about potential changed status or conditions.

Figure 5:
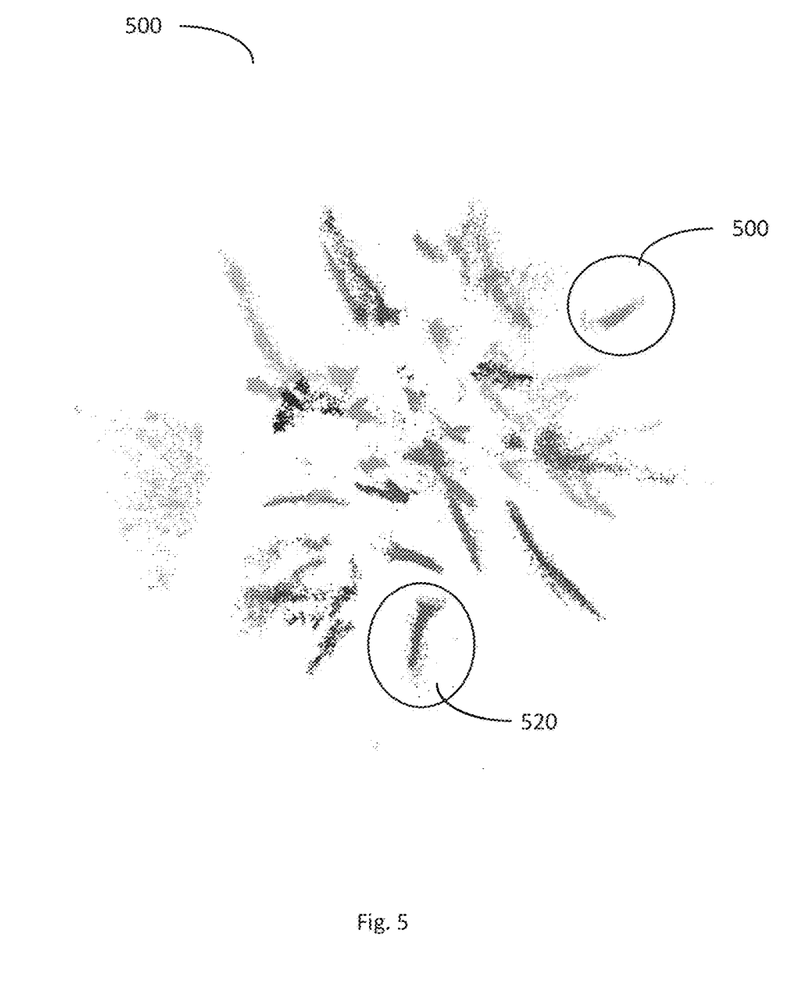
FIG. 5 illustrates a chart illustrating example outputs of an identity analysis system, according to aspects of the disclosure.

FIG. 5 is a chart 500 depicting an exemplary output of the latent space parameterization of electrocardiogram recordings from a plurality of individuals by an encoder. In some embodiments the latent space parameterization output that is generated by an encoder comprises an output generated by a variational auto-encoder. Each point in the chart 500 represents a single electrocardiogram recording. The variational auto-encoder clusters recordings from each individual into a specific area in the latent space. In some embodiments, the encoder may reduce the dimensionality of an electrocardiogram to more than two or three dimensions. However, in some embodiments clustering of users within the latent space may be processed in fewer dimensions. While additional clusters are present in the chart 500, clusters 520 and 510 are circled to demonstrate regions associated with two individuals in the set of electrocardiogram data. After a variational auto-encoder is trained on a set of training data, additional electrocardiograms associated with a new individual can also cluster in the latent space. The new individual can then be associated with a region in the latent space after a threshold number of electrocardiograms are input into the auto-encoder from the individual. When new recordings from an individual move outside the cluster represented by their training recordings, this may indicate a change in their electrocardiogram morphology outside of the normal variation for that individual.

In some embodiments that comprise an encoder, the encoding process may analyze the most or more salient and/or distinguishing characteristics of an electrocardiogram recording to assign a latent space value to reflect such salient and/or distinguishing characteristics. In this way, an electrocardiogram recording can be encoded into a series of latent space values, which may optionally be plotted in multi-dimensional space. In some embodiments, the number of latent space values used is 2, in which case a 2-dimensional plot may be assembled by plotting the latent space values along the X and Y axes. In some embodiments the number of latent space values used is 3, in which case a 3-dimensional plot may be assembled by plotting the latent space values along the X Y and Z axes. In some embodiments, electrocardiogram data and identity data is used to train the neural network while utilizing an encoder that translates electrocardiogram recordings and optionally identity data into any number of latent space variables. In this way, electrocardiogram groupings in latent space may correspond to the subject's trained identity data. For example, a subject may train the neural network by recording electrocardiogram measurements and providing corresponding information concerning the timing of administration of ibuprofen and the subject's temporal proximity to previous exercise. If a percentage of encoded electrocardiogram measurements fall within the same grouping while corresponding to the subject's administration of ibuprofen or exercise, a grouping may be designated as, for example, "subject's electrocardiogram recordings 100-5000 seconds following administration of ibuprofen" and/or "subject's electrocardiogram recordings 60-1200 seconds following exercise." In some embodiments identity data does not require encoding to be included in a multi-dimensional plot. For example, a subject may provide electrocardiogram recordings and identity data related to temporal proximity to previous sleep. In this case, all data is plotted onto a 3-dimensional plot, wherein the X and Y values are derived from encoded electrocardiogram recordings and the Z value relates to the time relative to the subject's last known sleep.

Figure 6:
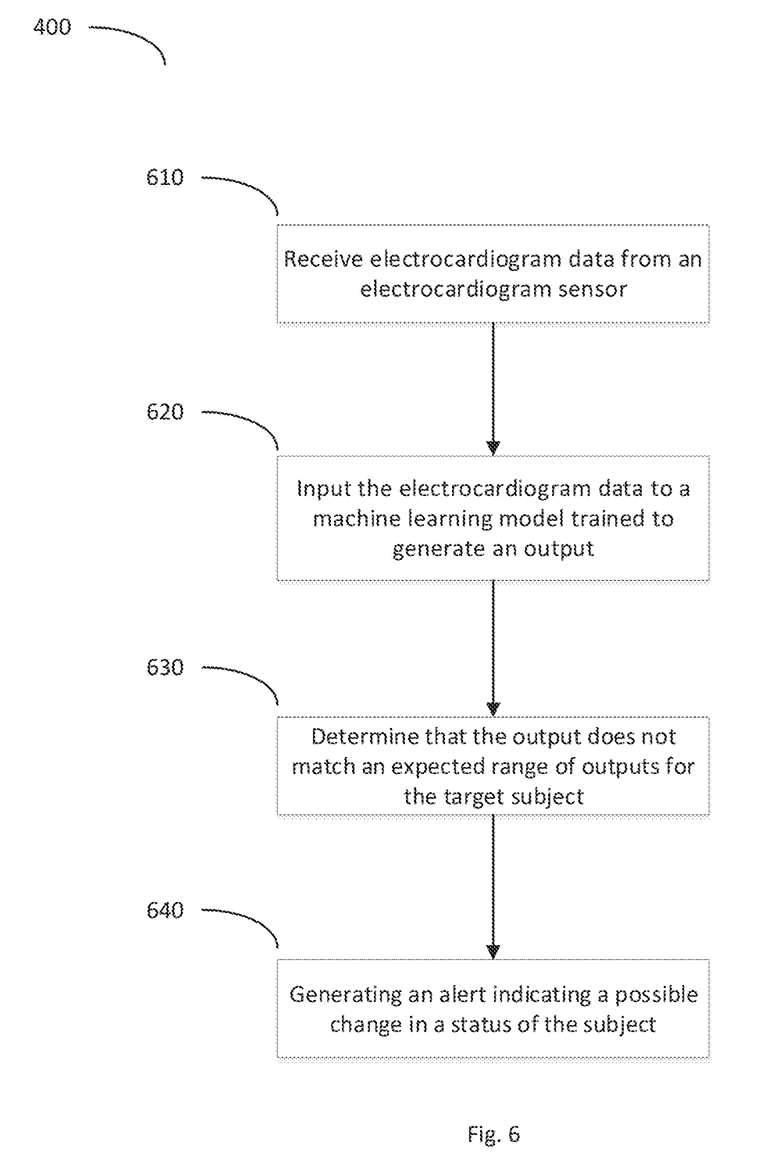
FIG. 6 illustrates flow diagram of processes as performed by an identity analysis system, according to aspects of the disclosure.

FIG. 6 depicts a flow chart 600 illustrating the application of a machine learning model to an electrocardiogram of a subject. In some embodiments, the processes described with respect to FIG. 4 may be performed by one or more components of the identity analysis system 110 as described with reference to FIG. 1.

Beginning in block 610, an identity analysis system may receive electrocardiogram data from an electrocardiogram sensor. For example, the electrocardiogram sensor may provide real-time data of an individual's heartbeats. In some embodiments, the electrocardiogram sensor may be a 1 lead sensor, a 2 lead sensor, a 3 lead sensor, a 4 lead sensor, a 6 lead sensor, or a 12 lead sensor. In some embodiments, the identity analysis system may utilize only a subset of the electrocardiogram data that is received.

In block 620, the identity analysis system may input the received electrocardiogram into a machine learning model to generate an output based on the electrocardiogram. In some embodiments, the machine learning model has been trained on electrocardiogram data labeled as belonging to the target subject or to other individuals. In some embodiments, the machine learning model may be an auto-encoder trained on electrocardiograms from a population of individuals. The machine learning model can then determine a latent space representation of the received electrocardiogram. The output of the machine learning model can then be used to determine if the electrocardiogram matches a predicted region in the latent space for the target individual.

In block 630, the identity analysis system determines whether the generated output does or does not match an expected range of outputs or threshold for the target subject. For example, the output of the machine learning model can be a probability that the identity matches the identity of the target subject. If the identity analysis system determines that the probability is under a threshold value, the system can determine that the output does not match the identity of the target subject.

In block 640, in response to the output not matching the expected range of outputs for the target subject, the identity analysis system can generate an alert indicating a possible change in a status of the target subject. For example, the alert can be provided to the target subject, to a medical practitioner, to a family member, to another associated individual, or any combination thereof. In some embodiments, the alert can be provided to the user over a user interface to confirm the identity of the individual.

Figure 7:
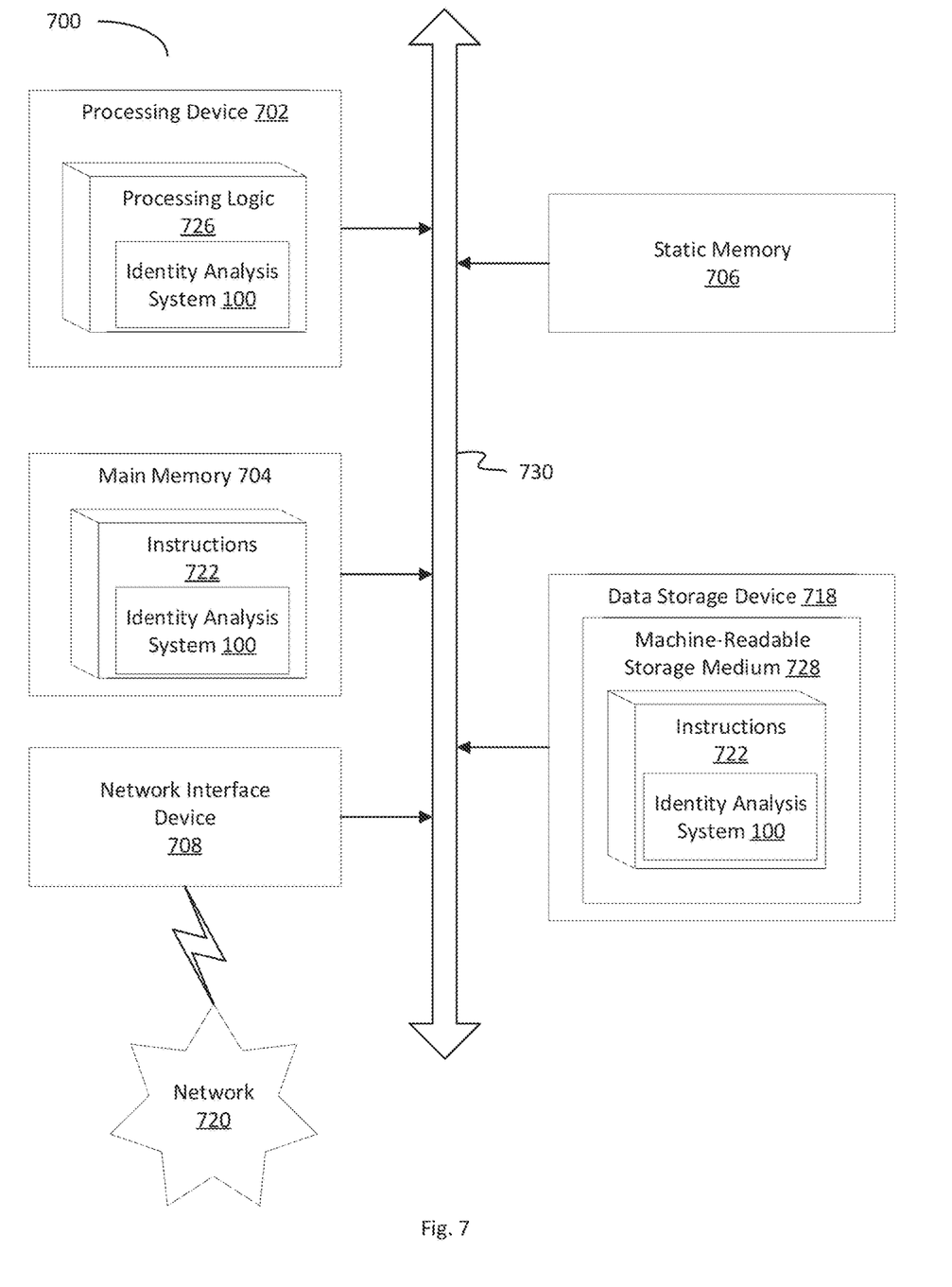
FIG. 7 illustrates an example computing environment of an Identity analysis system, according to aspects of the disclosure.

FIG. 7 illustrates a diagrammatic representation of a machine in the example of a computer system 700 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, wearable computing device, a set-top box (STB), a personal digital assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server, such as one or more components of identity analysis system 110 configured to perform processes as described above.

The exemplary computer system 700 includes a processing device 702, a main memory 704 (e.g., read-only memory (ROM), flash memory, dynamic random access memory (DRAM), a static memory 706 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute processing logic 726, which may be one example of system 400 shown in FIG. 4, for performing the operations and steps discussed herein.

The data storage device 718 may include a machine-readable storage medium 728, on which is stored one or more set of instructions 722 (e.g., software) embodying any one or more of the methodologies of functions described herein, including instructions to cause the processing device 702 to execute identity analysis systems 110. The instructions 722 may also reside, completely or at least partially, within the main memory 704 or within the processing device 702 during execution thereof by the computer system 700; the main memory 704 and the processing device 702 also constituting machine-readable storage media. The instructions 722 may further be transmitted or received over a network 720 via the network interface device 708.

The machine-readable storage medium 728 may also be used to store instructions to perform a method for identity analysis systems, as described herein. While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof

What is claimed is:

1. A method comprising:
   processing training data comprising a set of training electrocardiograms (ECGs) for each of a plurality of subjects using a machine learning model to generate an output for each training ECG of each of the plurality of subjects, wherein for each of the plurality of subjects, the set of training ECGs for the subject is labeled with an identity of the subject;
   training the machine learning model by comparing the output generated for each training ECG to a corresponding label of the training ECG to generate an identity model to identify ECGs of a first subject of the plurality of subjects;
   inputting a first ECG into the identity model, the identity model to generate an output indicating whether the first ECG corresponds to the first subject; and
   in response to the output indicating that the first ECG does not correspond to the first subject, determining based on the output, a condition that the first subject has or may develop.

2. The method of claim 1, wherein training ECGs for each of the plurality of subjects other than the first subject indicate a condition, and the machine learning model comprises an encoder that encodes the training ECGs of the first subject into a first region of a latent space and encodes the training ECGs for each of the plurality of subjects other than the first subject into a respective region of the latent space.

3. The method of claim 2, wherein generating the output indicating whether the first ECG corresponds to the first subject comprises:
encoding the first ECG into a first position within the latent space; and
determining whether the first position is within the first region of the latent space.

4. The method of claim 3, wherein determining based on the output, the condition that the first subject has or may develop comprises:
determining a vector represented by a difference in the first position relative to a position within the latent space of each of the training ECGs for each of the plurality of other subjects.

5. The method of claim 2, wherein the output indicating whether the first ECG corresponds to the first subject comprises a probability that the first ECG corresponds to the first subject.

6. The method of claim 5, wherein the probability that the first ECG corresponds to the first subject is based on a proximity of the first position to the first region of the latent space.

7. The method of claim 2, wherein the machine learning model comprises a variational autoencoder.

8. A system comprising:
an electrocardiogram (ECG) sensor;
a memory; and
a processing device operatively coupled to the memory, the processing device to:
process training data comprising a set of training ECGs for each of a plurality of subjects using a machine learning model to generate an output for each training ECG of each of the plurality of subjects, wherein for each of the plurality of subjects, the set of training ECGs for the subject is labeled with an identity of the subject;
train the machine learning model by comparing the output generated for each training ECG to a corresponding label of the training ECG to generate an identity model to identify ECGs of a first subject of the plurality of subjects;
receive, from the ECG sensor, a first ECG;
process the first ECG using the identity model, the identity model to generate an output indicating whether the first ECG corresponds to the first subject; and
in response to the output indicating that the first ECG does not correspond to the first subject, determine based on the output, a condition that the first subject has or may develop.

9. The system of claim 8, wherein training ECGs for each of the plurality of subjects other than the first subject indicate a condition, and the machine learning model comprises an encoder that encodes the training ECGs of the first subject into a first region of a latent space and encodes the training ECGs for each of the plurality of subjects other than the first subject into a respective region of the latent space.

10. The system of claim 9, wherein to generate the output indicating whether the first ECG corresponds to the first subject, the processing device is to:
encode the first ECG into a first position within the latent space; and
determine whether the first position is within the first region of the latent space.

11. The system of claim 10, wherein to determine based on the output, the condition that the first subject has or may develop, the processing device is to:
determine a vector represented by a difference in the first position relative to a position within the latent space of each of the training ECGs for each of the plurality of other subjects.

12. The system of claim 9, wherein the output indicating whether the first ECG corresponds to the first subject comprises a probability that the first ECG corresponds to the first subject.

13. The system of claim 12, wherein the probability that the first ECG corresponds to the first subject is based on a proximity of the first position to the first region of the latent space.

14. The system of claim 9, wherein the machine learning model comprises a variational autoencoder.

15. A non-transitory computer-readable medium having instructions stored thereon which, when executed by a processing device, cause the processing device to:
process training data comprising a set of training electrocardiograms (ECGs) for each of a plurality of subjects using a machine learning model to generate an output for each training ECG of each of the plurality of subjects, wherein for each of the plurality of subjects, the set of training ECGs for the subject is labeled with an identity of the subject;
train the machine learning model by comparing the output generated for each training ECG to a corresponding label of the training ECG to generate an identity model to identify ECGs of a first subject of the plurality of subjects;
input a first ECG into the identity model, the identity model to generate an output indicating whether the first ECG corresponds to the first subject; and
in response to the output indicating that the first ECG does not correspond to the first subject, determine based on the output, a condition that the first subject has or may develop.

16. The non-transitory computer-readable medium of claim 15, wherein training ECGs for each of the plurality of subjects other than the first subject indicate a condition, and the machine learning model comprises an encoder that encodes the training ECGs of the first subject into a first region of a latent space and encodes the training ECGs for each of the plurality of subjects other than the first subject into a respective region of the latent space.

17. The non-transitory computer-readable medium of claim 16, wherein to generate the output indicating whether the first ECG corresponds to the first subject, the processing device is to:
encode the first ECG into a first position within the latent space; and
determine whether the first position is within the first region of the latent space.

18. The non-transitory computer-readable medium of claim 17, wherein to determine based on the output, the condition that the first subject has or may develop, the processing device is to:
determine a vector represented by a difference in the first position relative to a position within the latent space of each of the training ECGs for each of the plurality of other subjects.

19. The non-transitory computer-readable medium of claim 16, wherein the output indicating whether the first ECG corresponds to the first subject comprises a probability that the first ECG corresponds to the first subject.

20. The non-transitory computer-readable medium of claim 19, wherein the probability that the first ECG corresponds to the first subject is based on a proximity of the first position to the first region of the latent space.

* * * * *